(12) United States Patent
Ishikawa et al.

(10) Patent No.: US 12,006,398 B2
(45) Date of Patent: Jun. 11, 2024

(54) POLYCARBONATE RESIN

(71) Applicant: MITSUBISHI GAS CHEMICAL COMPANY, INC., Tokyo (JP)

(72) Inventors: Shun Ishikawa, Ibaraki (JP); Noriyoshi Ogawa, Ibaraki (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 514 days.

(21) Appl. No.: 17/598,531

(22) PCT Filed: Mar. 30, 2020

(86) PCT No.: PCT/JP2020/014513
§ 371 (c)(1),
(2) Date: Sep. 27, 2021

(87) PCT Pub. No.: WO2020/203958
PCT Pub. Date: Oct. 8, 2020

(65) Prior Publication Data
US 2022/0177644 A1    Jun. 9, 2022

(30) Foreign Application Priority Data

Apr. 2, 2019    (JP) .................. 2019-070650

(51) Int. Cl.
| | | |
|---|---|---|
| *C08G 64/14* | (2006.01) | |
| *C07D 249/20* | (2006.01) | |
| *C08G 64/00* | (2006.01) | |
| *C08G 64/24* | (2006.01) | |
| *C08G 64/42* | (2006.01) | |

(52) U.S. Cl.
CPC .......... *C08G 64/14* (2013.01); *C07D 249/20* (2013.01); *C08G 64/00* (2013.01); *C08G 64/24* (2013.01); *C08G 64/42* (2013.01)

(58) Field of Classification Search
CPC ...... C08G 64/00; C08G 64/045; C08G 64/12; C08G 64/14; C08G 64/24; C08G 64/42; C07D 249/20
See application file for complete search history.

(56) References Cited

U.S. PATENT DOCUMENTS

| | | | |
|---|---|---|---|
| 4,153,780 A | 5/1979 | Narita et al. | |
| 4,221,645 A | 9/1980 | Adelmann et al. | |
| 5,523,379 A | 6/1996 | Rosenquist | |
| 6,096,852 A * | 8/2000 | Lensvelt ................ | C08K 5/134 |
| | | | 528/196 |

FOREIGN PATENT DOCUMENTS

| | | |
|---|---|---|
| CN | 104193979 A | 12/2014 |
| EP | 0 187 248 B1 | 11/1985 |
| JP | 49-99596 A | 9/1974 |
| JP | 55-9696 A | 1/1980 |
| JP | 61-141726 A | 6/1986 |
| JP | 6-145491 A | 5/1994 |
| JP | 6-256493 A | 9/1994 |
| JP | 8-253575 A | 10/1996 |
| JP | 9-316187 A | 12/1997 |
| JP | 2002-179902 A | 6/2002 |
| KR | 101607014 B1 | 3/2016 |

OTHER PUBLICATIONS

Extended European Search Report issued in European Patent Application No. 20784776.5 dated Apr. 12, 2022.
International Search Report issued in International Patent Application No. PCT/JP2020/014513, dated Jun. 16, 2020, along with English translation thereof.
Written Opinion of the International Searching Authority issued in International Patent Application No. PCT/JP2020/014513, dated Jun. 16, 2020, along with English translation thereof.

* cited by examiner

*Primary Examiner* — Kregg T Brooks
*Assistant Examiner* — David R. Foss
(74) *Attorney, Agent, or Firm* — GREENBLUM & BERNSTEIN P.L.C.

(57) ABSTRACT

A terminally modified polycarbonate resin that has ultraviolet absorbing capability is provided. More specifically, the terminally modified polycarbonate resin has a structure represented by general formula (A) and a constituent unit that is derived from a dihydric phenol. (In general formula (A), $R_1$ represents a hydrogen atom or an alkyl group having 1-6 carbon atoms; $R_2$ represents an alkylene group having 1-6 carbon atoms; $R_3$ represents a hydrogen atom or a methyl group; $R_4$ represents a hydrogen atom or a halogen atom; and * represents the bonding position to the main chain of the polycarbonate resin.)

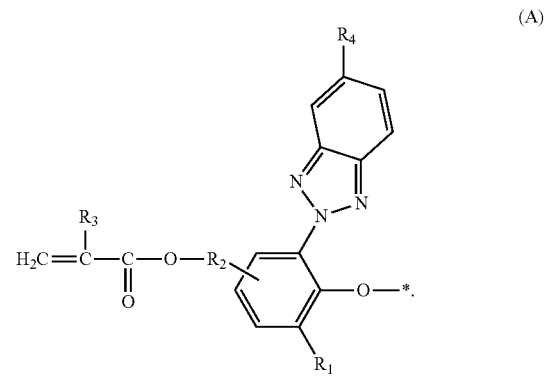

(A)

9 Claims, No Drawings

POLYCARBONATE RESIN

TECHNICAL FIELD

The present invention relates to a novel terminally modified polycarbonate resin.

BACKGROUND ART

Terminally reactive polycarbonates include polycarbonates having a vinyl end group or a conjugated double bond (Patent documents 1 and 2). These polycarbonates have an ultraviolet absorbing capacity but are highly reactive. Therefore, they have a drawback in that they are even reactive and polymerized by ultraviolet light outside, whereby they lose their activity and function as a UV absorber. Moreover, a polycarbonate having a triazole or benzophenone-based UV absorber bound to its end is known (Patent document 3). Such UV absorber shows excellent weatherability but has low activity as a reactive group and thus is not suitable to be used as a raw material for producing a block copolymer with other resin or as a reactive resin modifier.

As terminally modified polycarbonate resins, a terminally modified polycarbonate oligomer terminated with a chalcone derivative (Patent document 4), a polycarbonate resin having an end group with a specific structure including a benzotriazole ring (Patent document 5), and the like are known but further development of terminally modified polycarbonate resins is desired.

PRIOR ART DOCUMENTS

Patent Documents

Patent document 1: JP S55-9696 A
Patent document 2: JP S61-141726 A
Patent document 3: JP S49-99596 A
Patent document 4: JP H6-256493 A
Patent document 5: JP H9-316187 A

SUMMARY OF INVENTION

Problem to be Solved by the Invention

Development of a novel terminally modified polycarbonate resin having an excellent UV absorbing capacity is desired.

Means for Solving the Problem

The present inventors have gone through extensive studies and as a result of which developed a novel terminally modified polycarbonate resin having an excellent UV absorbing capacity, thereby accomplishing the present invention.

Thus, the present invention comprises the following embodiments.

(1) A terminally modified polycarbonate resin comprising a structure represented by General formula (A) and a structural unit derived from a dihydric phenol:

[Chemical formula 1]

(A)

(in General formula (A) above, $R_1$ represents a hydrogen atom or a C1-C6 alkyl group, $R_2$ represents a C1-C6 alkylene group, $R_3$ represents a hydrogen atom or a methyl group, $R_4$ represents a hydrogen atom or a halogen atom, and * represents the position of the bond to the main chain of the polycarbonate resin.)

(2) The terminally modified polycarbonate resin according to (1) above, wherein the viscosity-average molecular weight is 10,000-60,000.

(3) The terminally modified polycarbonate resin according to either one of (1) and (2) above, comprising a structural unit represented by General formula (1) below which has an end group represented by General formula (A):

[Chemical formula 2]

(1)

(wherein, $R_5$-$R_8$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, and X is —O—, —S—, —SO—, —SO$_2$—, —CO— or a divalent group represented by any of General formulae (3) to (6) below:

[Chemical formula 3]

(3)

-continued

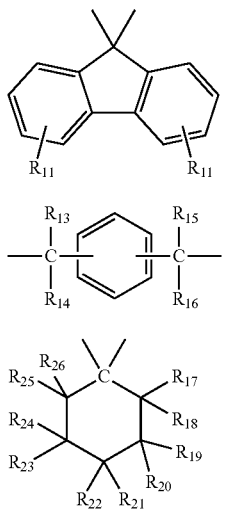

(4)

(5)

(6)

(in General formulae (3) to (6), $R_9$ and $R_{10}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_9$ and $R_{10}$ bind to each other to form a C3-C20 carbocyclic ring or a C1-C20 heterocyclic ring;

c represents an integer of 0-20;

$R_{11}$ and $R_{12}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_{11}$ and $R_{12}$ bind to each other to form a C3-C20 carbocyclic ring or a C1-C20 heterocyclic ring;

$R_{13}$-$R_{16}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_{13}$ and $R_{14}$, and $R_{15}$ and $R_{16}$ bind to each other to form a C3-C20 carbocyclic ring or a C1-C20 heterocyclic ring; and $R_{17}$-$R_{26}$ each independently represent a hydrogen atom or a C1-C3 alkyl group, where at least one of $R_{17}$-$R_{26}$ is a C1-C3 alkyl group.))

(4) The terminally modified polycarbonate resin according to (3) above, wherein X is a divalent group represented by General formula (3).

(5) The terminally modified polycarbonate resin according to either one of (3) and (4) above, wherein the dihydric phenol is a bisphenol compound.

(6) The terminally modified polycarbonate resin according to (5) above, wherein the bisphenol compound is selected from the group consisting of bisphenol A, bisphenol AP, bisphenol Z, bisphenol CD, bisphenol C, bisphenol IOTD, bisphenol IBTD and bisphenol MIBK.

(7) The terminally modified polycarbonate resin according to any one of (3) to (6) above, wherein the end structure represented by General formula (A) above is represented by Formula (7) below:

[Chemical formula 4]

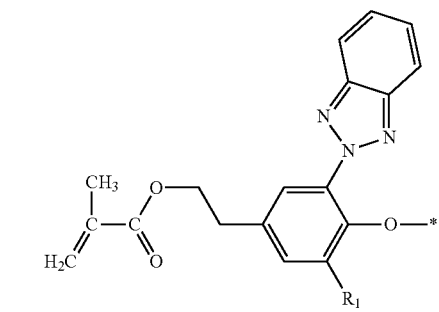

(7)

(in General formula (7), * represents the position of the bond to the main chain of the polycarbonate resin.)

(8) The polycarbonate resin according to any one of (1) to (7) above, which contains the end structure represented by General formula (A) in an amount of 0.5% or more by mass relative to the structural unit derived from a dihydric phenol.

(9) The polycarbonate resin according to any one of (1) to (8) above, wherein transmittance at 330 nm is 1% or less.

Effect of the Invention

The present invention can provide a novel terminally modified polycarbonate resin having an excellent UV absorbing capacity.

MODES FOR CARRYING OUT THE INVENTION

Hereinafter, the present invention will be described in detail.

1. Terminally Modified Polycarbonate Resin

The present invention provides a terminally modified polycarbonate resin comprising a structure represented by General formula (A) and a structural unit derived from a dihydric phenol:

[Chemical formula 5]

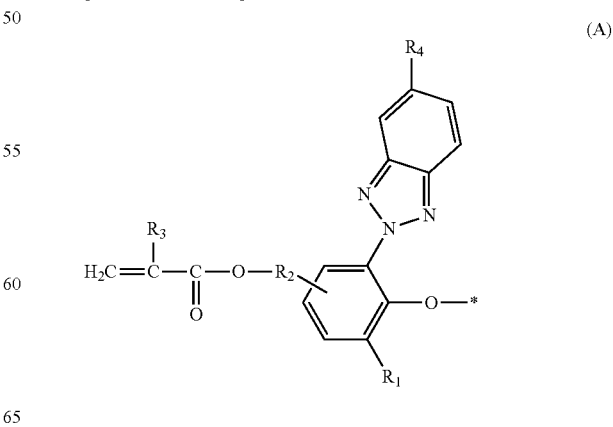

(A)

(in General formula (A) above, $R_1$ represents a hydrogen atom or a C1-C6 alkyl group, $R_2$ represents a C1-C6 alkylene group, $R_3$ represents a hydrogen atom or a methyl group, $R_4$ represents a hydrogen atom or a halogen atom, and * represents the position of the bond to the main chain of the polycarbonate resin.)

The terminally modified polycarbonate resin of the present invention may be a terminally modified polycarbonate resin having a structural unit represented by General formula (1) below which has an end group represented by General formula (A).

[Chemical formula 6]

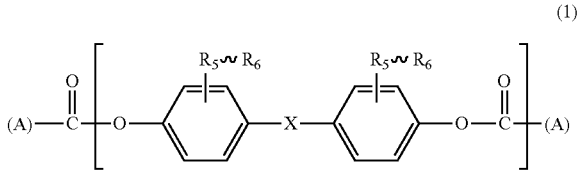

(wherein, $R_5$-$R_8$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, and X represents —O—, —S—, —SO—, —SO$_2$—, —CO— or a divalent group represented by any of General formulae (3) to (6) below:

[Chemical formula 7]

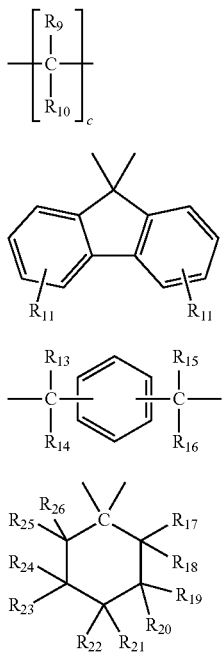

(in General formulae (3) to (6), $R_9$ and $R_{10}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_9$ and $R_{10}$ bind to each other to form a C3-C20 carbocyclic ring or a C1-C20 heterocyclic ring;

c represents an integer of 0-20;

$R_{11}$ and $R_{12}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_{11}$ and $R_{12}$ bind to each other to form a C3-C20 carbocyclic ring or a C1-C20 heterocyclic ring;

$R_{13}$-$R_{16}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_{13}$ and $R_{14}$, and $R_{15}$ and $R_{16}$ bind to each other to form a C3-C20 carbocyclic ring or a C1-C20 heterocyclic ring; and $R_{17}$-$R_{26}$ each independently represent a hydrogen atom or a C1-C3 alkyl group, where at least one of $R_{17}$-$R_{26}$ is a C1-C3 alkyl group.))

In one embodiment of the present invention, X of the structural unit represented by General formula (1) above may be a divalent group represented by General formula (3).

In one embodiment of the present invention, the dihydric phenol may be a bisphenol compound. According to the present invention, examples of the bisphenol compound used as the dihydric phenol include, but not limited to, 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, 1,1-bis(4-hydroxyphenyl)-1-phenylethane, bis(4-hydroxyphenyl)diphenylmethane, α,ω-bis[3-(O-hydroxyphenyl)propyl]polydimethylsiloxane, 2,2-bis(4-hydroxyphenyl)propane (bisphenol A; BPA), 1,1-bis(4-hydroxyphenyl)-1-phenylethane (bisphenol AP), 2,2-bis(4-hydroxyphenyl)butane (bisphenol B; BPB), bis(4-hydroxyphenyl)diphenylmethane (bisphenol BP), bisphenol CD, 2,2-bis(3-methyl-4-hydroxyphenyl)propane (bisphenol C), 1,1-bis(4-hydroxyphenyl)ethane (bisphenol E), bis(4-hydroxyphenyl)methane (bisphenol F), 2,2-bis(4-hydroxy-3-isopropylphenyl)propane (bisphenol G), 1,1-bis(4-hydroxyphenyl)-2-ethylhexane (bisphenol IOTD), 1,1-bis(4-hydroxyphenyl)-2-methylpropane (bisphenol IBTD), 1,1-bis(4-hydroxyphenyl)-2-methylpentane (bisphenol MIBK), 5,5'-(1-methylethylidene)-bis[1,1'-(bisphenyl)-2-ol]propane (bisphenol PH), 1,1-bis(4-hydroxyphenyl)-3,3,5-trimethylcyclohexane (bisphenol TMC) and 1,1-bis(4-hydroxyphenyl)cyclohexane (bisphenol Z; BPZ). In a preferred embodiment of the present invention, the bisphenol compound may be selected from the group consisting of bisphenol A, bisphenol AP, bisphenol Z, bisphenol CD, bisphenol C, bisphenol IOTD, bisphenol IBTD and bisphenol MIBK. In one embodiment of the present invention, a single kind of dihydric phenol mentioned above may be used alone or two or more kinds of them may be used in combination.

A monohydric phenol (also referred to as "Terminating agent A"), which is a precursor of the structure represented by General formula (A) above is commercially available as a UV absorber. In one embodiment of the present invention, a single kind of monohydric phenol mentioned above may be used alone or two or more kinds of them may be used in combination.

In a preferred embodiment of the present invention, the end structure represented by General formula (A) above may be a structure represented by Formula (7) below.

[Chemical formula 8]

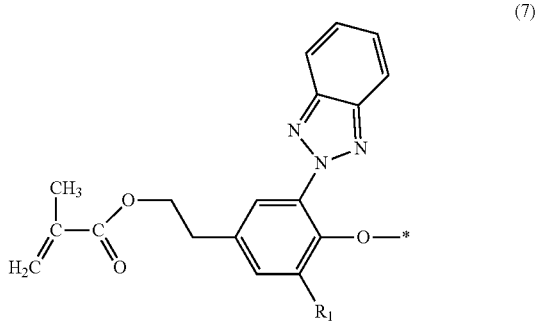

(7)

(in General formula (7), *represents the position of the bond to the main chain of the polycarbonate resin.)

In one embodiment of the present invention, the end structure represented by General formula (A) above may be contained in an amount of preferably 0.5%-15% by mass relative to the above-described structural unit derived from a dihydric phenol. The end structure represented by General formula (A) above may be contained in an amount of more preferably 1%-10% by mass, still more preferably 2%-10% by mass, and particularly preferably 3%-7% by mass relative to the above-described structural unit derived from a dihydric phenol.

In one embodiment of the present invention, the terminally modified polycarbonate resin may comprise any of a random copolymer structure, a block copolymer structure or an alternating copolymer structure.

In one embodiment of the present invention, the terminally modified polycarbonate resin can be blended with other resin to give a terminally modified polycarbonate resin composition. Examples of other resin include, but not limited to, polyamide, polyacetal, polycarbonate, a modified polyphenylene ether, polyethylene terephthalate and polybutylene terephthalate.

In one embodiment of the present invention, the terminally modified polycarbonate resin may be added with an antioxidant and a mold release agent as an additive to give a terminally modified polycarbonate resin composition.

Examples of the antioxidant include triethylene glycol-bis[3-(3-tert-butyl-5-methyl-4-hydroxyphenyl)propionate], 1,6-hexanediol-bis[3-(3,5-di-tert-butyl-4-hydroxyphenyl) propionate], pentaerythritol-tetrakis[3-(3,5-di-tert-butyl-4-hydroxyphenyl)propionate], octadecyl-3-(3,5-di-tert-butyl-4-hydroxyphenyl)propionate, 1,3,5-trimethyl-2,4,6-tris(3,5-di-tert-butyl-4-hydroxybenzyl)benzene, N,N-hexamethylenebis(3,5-di-tert-butyl-4-hydroxy-hydrocinnamide), 3,5-di-tert-butyl-4-hydroxy-benzylphosphonate-diethylester, tris(3,5-di-tert-butyl-4-hydroxybenzyl)isocyanurate and 3,9-bis {1,1-dimethyl-2-[β-(3-tert-butyl-4-hydroxy-5-methylphenyl)propionyloxy]ethyl}-2,4,8,10-tetraoxaspiro (5,5)undecane.

The content of the above-described antioxidant in the terminally modified polycarbonate resin composition is preferably 0.50% or less by mass, more preferably 0.10%-0.40% by mass, and particularly preferably 0.20%-0.40% by mass.

The mold release agent is preferably one that contains an ester resulting from an alcohol and a fatty acid in an amount of 90% or more by mass. Examples of the ester resulting from an alcohol and a fatty acid specifically include an ester resulting from a monohydric alcohol and a fatty acid, and a partial or whole ester resulting from a polyhydric alcohol and a fatty acid. The ester resulting from a monohydric alcohol and a fatty acid described above is preferably an ester resulting from a monohydric alcohol having 1-20 carbon atoms and a saturated fatty acid having 10-30 carbon atoms. Moreover, a partial or whole ester resulting from a polyhydric alcohol and a fatty acid is preferably a partial or whole ester resulting from a polyhydric alcohol having 1-25 carbon atoms and a saturated fatty acid having 10-30 carbon atoms.

Examples of the ester resulting from a monohydric alcohol and a saturated fatty acid specifically include stearyl stearate, palmityl palmitate, butyl stearate, methyl laurate and isopropyl palmitate. Examples of the partial or whole ester resulting from a polyhydric alcohol and a saturated fatty acid include glycerol monostearate, glycerol monostearate, glycerol distearate, glycerol tristearate, sorbitan monostearate, glycerol monobehenate, glycerol monocaprylate, glycerol monolaurate, pentaerythritol monostearate, pentaerythritol tetrastearate, pentaerythritol tetrapelargonate, propylene glycol monostearate, biphenyl biphenate, sorbitan monostearate, 2-ethylhexyl stearate, and partial or whole esters of dipentaerythritol such as dipentaerythritol hexastearate.

The content of the above-described mold release agent in the terminally modified polycarbonate resin composition is preferably 0.50% or less by mass, more preferably 0.01%-0.10% by mass, and particularly preferably 0.03%-0.05% by mass.

Furthermore, the terminally modified polycarbonate resin composition of the present invention may be added with other additive(s) such as a processing stabilizer, a UV absorber, a fluidity modifier, a crystal nucleating agent, a reinforcing agent, a dye, an antistatic agent, a bluing agent, an antibacterial agent or the like.

2. Method for Producing Terminally Modified Polycarbonate Resin

In one embodiment of the present invention, the terminally modified polycarbonate resin can be produced by a method employed for producing conventional polycarbonate resins except that a terminating agent is used.

Specifically, in a case of an interfacial polymerization method, a dihydric phenol-based compound and phosgene are allowed to react with each other in the presence of an inert organic solvent and an aqueous alkaline solution, and then a terminating agent and a polymerization catalyst such as a tertiary amine or a quaternary ammonium salt are added to allow polymerization. In a case of a pyridine method, a dihydric phenol-based compound and a terminating agent are dissolved in pyridine or a mixed solution of pyridine and an inert solvent, into which phosgene is blown to directly obtain a polycarbonate oligomer. According to the interfacial polymerization method, the above-described terminating agent may be added upon reaction between the dihydric phenol-based compound and phosgene.

3. Physical Properties of Terminally Modified Polycarbonate Resin (A) Viscosity-Average Molecular Weight (Mv)

In one embodiment of the present invention, the viscosity-average molecular weight (Mv) of the terminally modified polycarbonate resin may preferably be 10,000-60,000. The viscosity-average molecular weight (Mv) of the terminally modified polycarbonate is more preferably 13,000-50,000, still more preferably 15,000-40,000, yet still more preferably 20,000-35,000, and particularly preferably 25,300-33,500. As far as the viscosity-average molecular weight (Mv) of the polycarbonate lies within the aforementioned range, the molded body can be prevented from becoming brittle, the melt viscosity can be prevented from becoming too high so that the produced resin can be taken out easily, and the fluidity can be improved to facilitate injection molding in a molten state.

The viscosity-average molecular weight (Mv) was calculated by the following equation:

$$\eta = 1.23 \times 10^{-4} \times Mv^{0.83}$$

where the intrinsic viscosity [η](deciliters/gram) was determined under the following measurement conditions at a Huggins constant of 0.45:
  Measurement instrument: Ubbelohde capillary viscometer
  Solvent: Dichloromethane
  Concentration of resin solution: 0.5 grams/deciliter
  Measurement temperature: 25° C.
(B) Transmittance at 330 nm
In one embodiment of the present invention, the transmittance at 330 nm of the terminally modified polycarbonate resin may be 1% or less. The transmittance at 330 nm of the terminally modified polycarbonate resin of the present invention may be preferably 0.5% or less, and more preferably 0.1% or less. As far as the transmittance at 330 nm lies within the above-mentioned range, the terminally modified polycarbonate resin can be put to practical use as a polycarbonate resin excellent in both UV absorbing capacity and photostability.

The transmittance at 330 nm was obtained by conducting zero adjustment at 330 nm with a dichloromethane solvent, and then measuring transmittance of the resin solution under the following conditions:
  Measurement instrument: UV-visible spectrophotometer UV-1280 manufactured by Shimadzu Corporation
  Solvent: Dichloromethane
  Concentration of resin solution: 10% (w/w)
  Cell: 1 cm quartz cell
  Photometric mode
(C) Infrared Absorption (IR) Spectroscopy
Absorptions of C=N stretching and N=N stretching originating from Terminating agent A were confirmed at 1640 cm$^{-1}$ and 1720 cm$^{-1}$ in the IR spectrum, confirming incorporation of the terminating agent at the end of the polycarbonate resin.

The IR spectrum was obtained by conducting measurement in the measured wavenumber range of 4000-650 cm$^{-1}$ by a film technique using FT/IR-400+ manufactured by JASCO Corporation. The film was prepared by a solution-cast film technique by dissolving the polycarbonate resin in dichloromethane.

EXAMPLES

Hereinafter, the present invention will be described by way of examples. These examples are not intended to limit the present invention.
<Production of Terminally Modified Polycarbonate Resins and Analyses of their Physical Properties>
Terminally modified polycarbonate resins were produced by the following methods to analyze the viscosity-average molecular weight (Mv), the transmittance at 330 nm and the infrared absorption (IR) spectrum of each of the resulting resins.

Example 1

To 600 ml of a 9% (w/w) aqueous sodium hydroxide solution and 200 ml of pure water, 100 g of bisphenol A (BPA) manufactured by NIPPON STEEL Chemical and Material Co., Ltd. and 0.5 g hydrosulfite were added to be dissolved therein. To this, 330 ml of dichloromethane was added, and 59.7 g of phosgene was blown into the resultant by spending 30 minutes while stirring and keeping the solution temperature within a range of 15-25° C.

After the end of phosgene blowing, 100 ml of a 9% (w/w) aqueous sodium hydroxide solution, 200 ml of dichloromethane and 3.3 g of RUVA-93 manufactured by Otsuka Chemical Co., Ltd. (Terminating agent A) dissolved in 50 ml of dichloromethane were added and vigorously stirred to emulsify, followed by addition of 0.5 ml of triethylamine (TEA) as a polymerization catalyst to allow polymerization for about 40 minutes.

[Chemical formula 9]

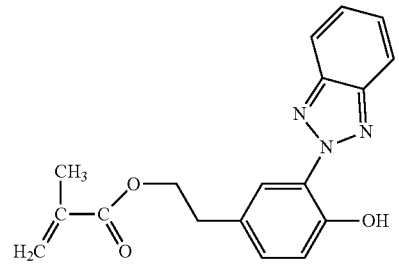

RUVA-93

[Chemical formula 10]

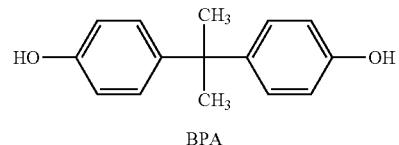

BPA

The polymerization solution was separated into an aqueous phase and an organic phase. The organic phase was neutralized with phosphoric acid and repeatedly washed with pure water until pH of the rinsing liquid was neutral. The organic solvent was evaporated and distilled away from the resulting polycarbonate resin solution, thereby obtaining polycarbonate resin powder.
(Results of Analyses)
My was 33,500, and transmittance at 330 nm was 0.1%. Furthermore, absorptions of C=N stretching and N=N stretching originating from Terminating agent A were confirmed at 1640 cm$^{-1}$ and 1720 cm$^{-1}$ in the IR spectrum, confirming incorporation of the terminating agent at the end of the polycarbonate resin.

Example 2

A polycarbonate resin was synthesized in the same manner as Example 1 except that BPA was changed to 87 g of bisphenol AP manufactured by Honshu Chemical Industry Co., Ltd., and the amount of Terminating agent A was changed to 3.2 g.

[Chemical formula 11]

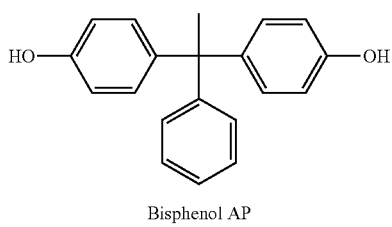

Bisphenol AP (Results of Analyses)

Mv was 27,200, and transmittance at 330 nm was 0.1%. As with Example 1, incorporation of the terminating agent at the end of the polycarbonate resin was confirmed in the IR spectrum.

Example 3

A polycarbonate resin was synthesized in the same manner as Example 1 except that BPA was changed to 90 g of bisphenol Z manufactured by Honshu Chemical Industry Co., Ltd., and the amount of Terminating agent A was changed to 3.6 g.

[Chemical formula 12]

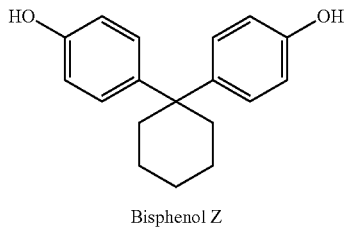

Bisphenol Z (Results of Analyses)

Mv was 22,300, and transmittance at 330 nm was 0.1%. As with Example 1, incorporation of the terminating agent at the end of the polycarbonate resin was confirmed in the IR spectrum.

Example 4

A polycarbonate resin was synthesized in the same manner as Example 1 except that BPA was changed to 130 g of bisphenol cyclododecane (bisphenol CD) manufactured by Honshu Chemical Industry Co., Ltd., and the amount of Terminating agent A was changed to 1.75 g.

[Chemical formula 13]

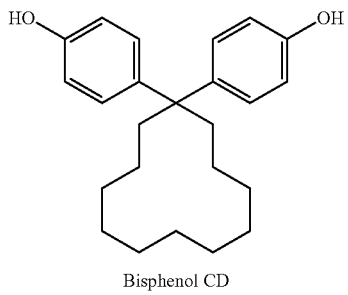

Bisphenol CD (Results of Analyses)

Mv was 33,500, and transmittance at 330 nm was 0.1%. As with Example 1, incorporation of the terminating agent at the end of the polycarbonate resin was confirmed in the IR spectrum.

Example 5

A polycarbonate resin was synthesized in the same manner as Example 1 except that 61.3 g of bisphenol C manufactured by Honshu Chemical Industry Co., Ltd. was used in addition to 41.2 g of BPA, and the amount of Terminating agent A was changed to 4.05 g.

[Chemical formula 14]

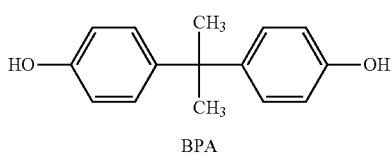

BPA

[Chemical formula 15]

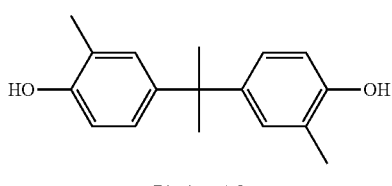

Bisphenol C (Results of Analyses)

Mv was 29,200, and transmittance at 330 nm was 0.1%. As with Example 1, incorporation of the terminating agent at the end of the polycarbonate resin was confirmed in the IR spectrum.

Example 6

A polycarbonate resin was synthesized in the same manner as Example 1 except that BPA was changed to 90 g of bisphenol MIBK manufactured by Honshu Chemical Industry Co., Ltd., and the amount of Terminating agent A was changed to 3.58 g.

[Chemical formula 16]

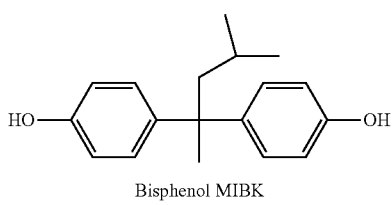

Bisphenol MIBK (Results of Analyses)

Mv was 25,300, and transmittance at 330 nm was 0.1%. As with Example 1, incorporation of the terminating agent at the end of the polycarbonate resin was confirmed in the IR spectrum.

Example 7

A polycarbonate resin was synthesized in the same manner as Example 1 except that BPA was changed to 90 g of bisphenol IOTD manufactured by Honshu Chemical Industry Co., Ltd., and the amount of Terminating agent A was changed to 3.25 g.

[Chemical formula 17]

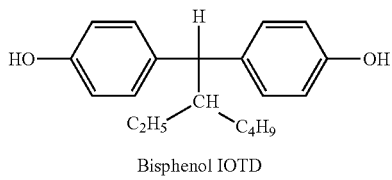

Bisphenol IOTD (Results of Analyses)
Mv was 26,600, and transmittance at 330 nm was 0.1%. As with Example 1, incorporation of the terminating agent at the end of the polycarbonate resin was confirmed in the IR spectrum.

Example 8

A polycarbonate resin was synthesized in the same manner as Example 1 except that BPA was changed to 80 g of bisphenol IBTD manufactured by Honshu Chemical Industry Co., Ltd., and the amount of Terminating agent A was changed to 3.55 g.

[Chemical formula 18]

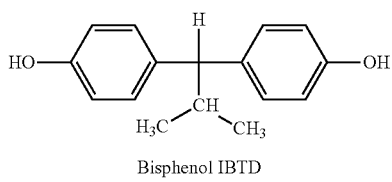

Bisphenol IBTD (Results of Analyses)
Mv was 25,200, and transmittance at 330 nm was 0.1%. As with Example 1, incorporation of the terminating agent at the end of the polycarbonate resin was confirmed in the IR spectrum.

Example 9

A polycarbonate resin was synthesized in the same manner as Example 1 except that BPA was changed to 100 g of bisphenol CD manufactured by Honshu Chemical Industry Co., Ltd. and 19.2 g bisphenol MIBK manufactured by Honshu Chemical Industry Co., Ltd., and the amount of Terminating agent A was changed to 4.41 g.

[Chemical formula 19]

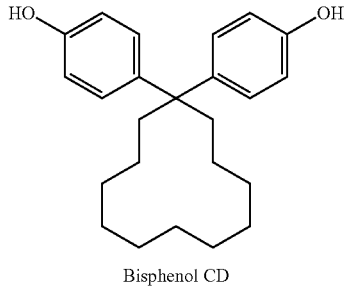

Bisphenol CD

[Chemical formula 20]

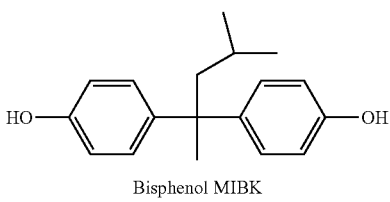

Bisphenol MIBK (Results of Analyses)
Mv was 18,200, and transmittance at 330 nm was 0.1%. As with Example 1, incorporation of the terminating agent at the end of the polycarbonate resin was confirmed in the IR spectrum.

Example 10

A polycarbonate resin was synthesized in the same manner as Example 9 except that the amount of Terminating agent A was changed to 7.17 g.
(Results of Analyses)
Mv was 13,200, and transmittance at 330 nm was 0.1%. As with Example 1, incorporation of the terminating agent at the end of the polycarbonate resin was confirmed in the IR spectrum.

Comparative Example 1

A polycarbonate resin was synthesized in the same manner as Example 1 except that Terminating agent A was changed to 1.55 g of p-tert-butylphenol (PTBP).

[Chemical formula 21]

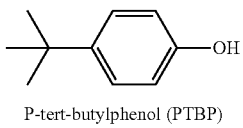

P-tert-butylphenol (PTBP)

(Results of Analyses)
Mv was 32,500, and transmittance at 330 nm was 98.3%. Absorptions at 1640 cm$^{-1}$ and 1720 cm$^{-1}$ were not confirmed in the IR spectrum.

Comparative Example 2

A polycarbonate resin was synthesized in the same manner as Example 5 except that Terminating agent A was changed to 1.73 g of MILEX PM (Terminating agent B) manufactured by Mitsui Chemicals, Inc.

[Chemical formula 22]

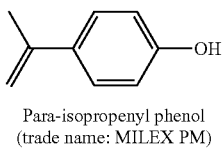

Para-isopropenyl phenol
(trade name: MILEX PM)

(Results of Analyses)

Mv was 24,100, and transmittance at 330 nm was 39.1%. Absorptions at 1640 cm$^{-1}$ and 1720 cm$^{-1}$ were not confirmed in the IR spectrum.

Comparative Example 3

A polycarbonate resin was synthesized in the same manner as Example 2 except that Terminating agent A was changed to 1.73 g of p-tert-butylphenol.

(Results of Analyses)

Mv was 21,000, and transmittance at 330 nm was 89.5%. Absorptions at 1640 cm$^{-1}$ and 1720 cm$^{-1}$ were not confirmed in the IR spectrum.

Comparative Example 4

A polycarbonate resin was synthesized in the same manner as Example 3 except that Terminating agent A was changed to 1.65 g of p-tert-butylphenol.

(Results of Analyses)

Mv was 20,000, and transmittance at 330 nm was 92.6%. Absorptions at 1640 cm$^{-1}$ and 1720 cm$^{-1}$ were not confirmed in the IR spectrum.

Comparative Example 5

A polycarbonate resin was synthesized in the same manner as Example 4 except that Terminating agent A was changed to 1.6 g of p-tert-butylphenol.

(Results of analyses)

Mv was 20,100, and transmittance at 330 nm was 76.7%. Absorptions at 1640 cm-1 and 1720 cm-1 were not confirmed in the IR spectrum.

The results of analyses described above are summarized in Table 1 below.

As can be appreciated from Table 1, the terminally modified polycarbonate resin of the present invention has an extremely low transmittance at 330 nm and an excellent UV absorbing capacity.

The invention claimed is:

1. A terminally modified polycarbonate resin comprising a structure represented by General formula (A) and a structural unit derived from a dihydric phenol:

[Chemical formula 1]

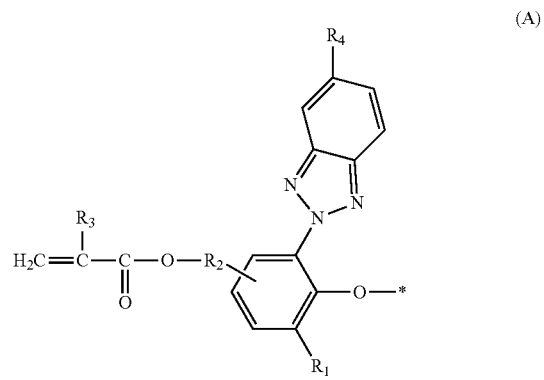

(A)

(in General formula (A) above, $R_1$ represents a hydrogen atom or a C1-C6 alkyl group, $R_2$ represents a C1-C6 alkylene group, $R_3$ represents a hydrogen atom or a methyl group, $R_4$ represents a hydrogen atom or a halogen atom, and * represents the position of the bond to the main chain of the polycarbonate resin).

2. The terminally modified polycarbonate resin according to claim 1, wherein the viscosity-average molecular weight is 10,000-60,000.

3. The terminally modified polycarbonate resin according to claim 1, comprising a structural unit represented by General formula (1) below which has an end group represented by General formula (A):

TABLE 1

|  | Dihydric phenol | Monohydric phenol | Mv | transmittance at 330 nm |
|---|---|---|---|---|
| Example 1 | BPA | Terminating agent A | 33,500 | 0.1% |
| Example 2 | Bisphenol AP | Terminating agent A | 27,200 | 0.1% |
| Example 3 | Bisphenol Z | Terminating agent A | 22,300 | 0.1% |
| Example 4 | Bisphenol CD | Terminating agent A | 33,500 | 0.1% |
| Example 5 | BPA Bisphenol C | Terminating agent A | 29,200 | 0.1% |
| Example 6 | Bisphenol MIBK | Terminating agent A | 25,300 | 0.1% |
| Example 7 | Bisphenol IOTD | Terminating agent A | 26,600 | 0.1% |
| Example 8 | Bisphenol IBTD | Terminating agent A | 25,200 | 0.1% |
| Example 9 | Bisphenol CD Bisphenol MIBK | Terminating agent A | 18,200 | 0.1% |
| Example 10 | Bisphenol CD Bisphenol MIBK | Terminating agent A | 13,200 | 0.1% |
| Comparative example 1 | BPA | PTBP | 32,500 | 98.3% |
| Comparative example 2 | BPA Bisphenol C | Terminating agent B | 24,100 | 39.1% |
| Comparative example 3 | Bisphenol AP | PTBP | 21,000 | 89.5% |
| Comparative example 4 | Bisphenol Z | PTBP | 20,000 | 92.6% |
| Comparative example 5 | Bisphenol CD | PTBP | 20,100 | 76.7% |

[Chemical formula 2]

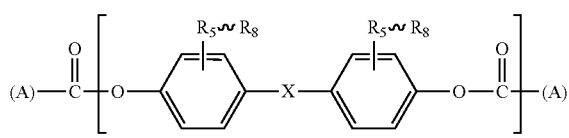

(wherein, $R_5$-$R_8$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, and X is —O—, —S—, —SO—, —SO$_2$—, —CO— or a divalent group represented by any of General formulae (3) to (6) below:

[Chemical formula 3]

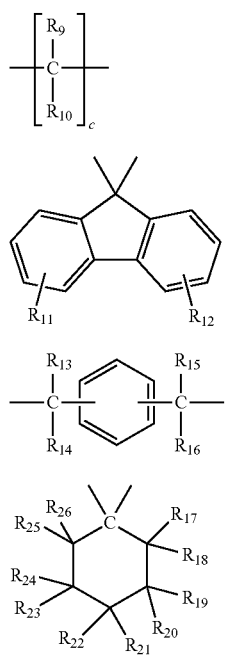

(in General formulae (3) to (6), $R_9$ and $R_{10}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_9$ and $R_{10}$ bind to each other to form a C3-C20 carbocyclic ring or a C1-C20 heterocyclic ring;

c represents an integer of 0-20;

$R_{11}$ and $R_{12}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_{11}$ and $R_{12}$ bind to each other to form a C3-C20 carbocyclic ring or a C1-C20 heterocyclic ring;

$R_{13}$-$R_{16}$ each independently represent a hydrogen atom, a halogen atom, an optionally substituted C1-C20 alkyl group, an optionally substituted C1-C5 alkoxy group, an optionally substituted C6-C12 aryl group, an optionally substituted C7-C17 aralkyl group or an optionally substituted C2-C15 alkenyl group, or $R_{13}$ and $R_{14}$, and $R_{15}$ and $R_{16}$ bind to each other to form a C3-C20 carbocyclic ring or a C1-C20 heterocyclic ring; and $R_{17}$-$R_{26}$ each independently represent a hydrogen atom or a C1-C3 alkyl group, where at least one of $R_{17}$-$R_{26}$ is a C1-C3 alkyl group)).

4. The terminally modified polycarbonate resin according to claim 3, wherein X is a divalent group represented by General formula (3).

5. The terminally modified polycarbonate resin according to claim 4, wherein the dihydric phenol is a bisphenol compound.

6. The terminally modified polycarbonate resin according to claim 5, wherein the bisphenol compound is selected from the group consisting of bisphenol A, bisphenol AP, bisphenol Z, bisphenol CD, bisphenol C, bisphenol IOTD, bisphenol IBTD and bisphenol MIBK.

7. The terminally modified polycarbonate resin according to claim 3, wherein the end structure represented by General formula (A) above is represented by Formula (7) below:

[Chemical formula 4]

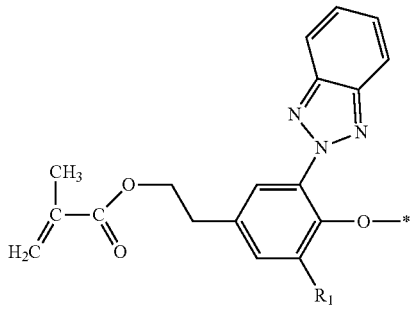

(in General formula (7), * represents the position of the bond to the main chain of the polycarbonate resin).

8. The polycarbonate resin according to claim 1, which contains the end structure represented by General formula (A) in an amount of 0.5% or more by mass relative to the structural unit derived from a dihydric phenol.

9. The polycarbonate resin according to claim 1, wherein transmittance at 330 nm is 1% or less.

* * * * *